United States Patent [19]

Imanaka et al.

[11] 4,266,053
[45] May 5, 1981

[54] MELAMINE GROUP-CONTAINING (METH)ACRYLATE

[75] Inventors: Yoshihiko Imanaka; Hiroshi Nakamatsu, both of Hino; Akihiro Horike, Musashino; Yoichi Saito; Kaoru Iwata, both of Hino, all of Japan

[73] Assignee: Teijin Limited, Osaka, Japan

[21] Appl. No.: 50,893

[22] Filed: Jun. 21, 1979

[30] Foreign Application Priority Data

| | | |
|---|---|---|
| Jun. 21, 1978 [JP] | Japan | 53/74117 |
| Jul. 5, 1978 [JP] | Japan | 53/80927 |
| Aug. 14, 1978 [JP] | Japan | 53/98218 |
| Sep. 22, 1978 [JP] | Japan | 53/115984 |

[51] Int. Cl.³ ............... C07D 251/70; C07D 251/64
[52] U.S. Cl. ..................................... 544/196; 544/197
[58] Field of Search ................................ 544/196, 197

[56] References Cited

U.S. PATENT DOCUMENTS

| | | | |
|---|---|---|---|
| 3,020,255 | 2/1962 | Magrane et al. | 260/45.3 |
| 3,047,532 | 7/1962 | D'Alelio | 544/196 |
| 3,165,515 | 1/1965 | D'Alelio | 544/196 |

FOREIGN PATENT DOCUMENTS

| | | | |
|---|---|---|---|
| 628150 | 8/1949 | United Kingdom. | |
| 968501 | 9/1964 | United Kingdom | 544/196 |

*Primary Examiner*—John M. Ford
*Attorney, Agent, or Firm*—Sughrue, Rothwell, Mion, Zinn and Macpeak

[57] ABSTRACT

The invention involves a novel melamine group-containing (meth)acrylate, e.g. hexakis(2-acryloyloxypropyl)melamine, hexakis(2-acryloyloxyethyl)melamine, etc., and its polymer. Said (meth)acrylate has excellent reactivity and storage stability, and said polymer has excellent dimensional stability, durabilities (especially water resistance and moisture resistance) and surface hardness, and is useful as a molded product and a coating layer of a molded resin article. For example, a polyester film coated with said polymer has excellent adhesivity, flexibility and dimensional stability as well as high abrasion resistance, and can be used to a wide variety of uses as an abrasion resistant film.

4 Claims, 6 Drawing Figures

MELAMINE GROUP-CONTAINING (METH)ACRYLATE

This invention relates to a novel melamine group-containing (meth)acrylate, a polymerizable (and curable) composition mainly composed of said melamine group-containing (meth)acrylate, a molded article of a polymer obtained by the polymerization of said composition, and a resin molded article coated at least a part of its surface with a polymer of a vinyl monomer composition mainly composed of said melamine group-containing (meth)acrylate.

A polyester synthesized from an aromatic dicarboxylic acid and an aliphatic diol, represented by polyethylene terephthalate, has excellent physical properties, such as mechanical and electrical properties, and can be applied to a wide variety of uses such as fiber, film, sheet and plastic; and a polycarbonate resin, as represented by bisphenol-A polycarbonate, is excellent in the mechanical, optical and electrical properties, and can be applied to a wide variety of uses as plastic, film, sheet, etc. Each of the polymers is known as an important polymer. Especially, the molded product of the latter polymer has excellent impact resistance and transparency, and is used as an organic glass, windshield, etc.

Since the surface of the molded product of the above polyester or polycarbonate is soft and low abrasion-resistant, it is easily damaged in the presence of dust or by scratching. The fine surface scratches make the surface cloudy and reduce the transparency and the gloss of the product.

Such a phenomenon often loses or remarkably reduces the practical value of the polymers, especially as film, sheet, plastic, etc., and that of polycarbonate as an organic glass.

In order to overcome these defects as an organic glass, polydiethylene glycol bis(allylcarbonate) has been developed recently, and used as eyeglasses, goggles, sunglasses, etc. The polymer is one of the plastics having highest hardness, and also has high transparency. The hardness of the polymer is, however, insufficient to the above applications, and the further improvement of the abrasion resistance is desired.

There are several known methods for the improvement of the abrasion resistance of such resin molded product; for example, organic coating with a thermosetting resin such as melamine resin, inorganic coating with an organo-polysiloxane, etc., and vacuum deposition of inorganic glass or $SiO_2$, etc. (Specifications of Japanese Pat. Laid-Open No. 52-25880, Japanese Pat. No. 53-39915, Japanese Pat. Laid-Open No. 52-97098, etc.) However, some of the organic coatings have only insufficient abrasion resistance, while others are not economical because of their poor workability and curability which necessitates a long-period heat-treatment at high temperature. Although the inorganic coatings generally have high hardness, there are several deficits such as poor applicability, generally low adhesivity which necessitates the primer treatment, and low elongation and flexibility which lead to the cracking by a severe deformation such as stretching and bending.

Furthermore, the vacuum deposition has a disadvantage of high vacuum evaporation cost as well as the deficits similar to those of the inorganic coating.

Therefore, there are few coating methods which satisfactorily give a coated product having not only high abrasion resistance but also excellent adhesivity, flexibility, dimensional stability and workability.

Meanwhile, the aforesaid melamine resin is, in addition to the above applications, useful as a decorative board, etc. taking advantage of its high hardness and heat resistance, and applied to table, desk, top board of kotatsu, and other furniture. Since the formation of the melamine resin is, similar to phenolic resin and urea resin, based on the condensation reaction with formaldehyde, the resin has some drawbacks such as (1) formation of by-products by the reaction, (2) high temperature and long time necessary for the reaction, and (3) poor storage stability.

As an attempt to correct the above drawbacks of melamine resin, a melamine group-containing (meth)acrylate obtained by the condensation of methylol melamine or methyl or butyl ether derivative of methylol melamine with a hydroxyl-containing (meth)acrylate is known (for example, refer to the specifications of British Pat. No. 628,150 and U.S. Pat. No. 3,020,255). The above drawbacks of melamine resin are corrected in such methylol melamine group-containing (meth)acrylate; however, the cured product thereof has other drawbacks of poor durability, especially resistance to water, such as moisture resistance, water (including hot water) resistance, etc., and is unsuitable for the use in contact with water or in a highly humid atmosphere. Therefore, the development of a compound free of the above drawbacks is highly desired.

It is an object of this invention to provide a novel melamine group-containing (meth)acrylate having excellent reactivity and storage stability and giving a polymer (cured product) having excellent durabilities (especially water resistance, moisture resistance, etc.), dimensional stability, hardness, transparency, surface smoothness, etc. Another object of this invention is to provide a polymerizable (and curable) composition mainly composed of said melamine group-containing (meth) acrylate and a molded article of a polymer obtained by the polymerization of said composition. It is a further object of this invention to provide a resin molded article coated at least a part of its surface with a vinyl polymer having excellent abrasion-resistance, transparency, surface smoothness, adhesivity, and flexibility, composed mainly of said melamine group-containing (meth)acrylate. Still further objects of this invention will become apparent as the following description proceeds.

The above objects can be achieved by the present invention which is characterized by the following descriptions:

1. A melamine group-containing (meth)acrylate of the general formula (I)

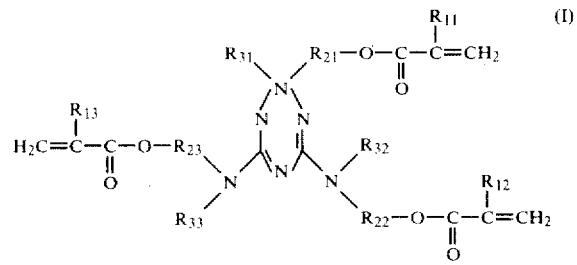

where $R_{11}$, $R_{12}$ and $R_{13}$ are each hydrogen atom or methyl group; $R_{21}$, $R_{22}$ and $R_{23}$ are each an alkylene group of from 2 to 10 carbon atoms, in which the number of carbon atoms in the main chain is 2 or more; and $R_{31}$, $R_{32}$ and $R_{33}$ are each hydrogen atom, a hydrocarbon group of from 1 to 10 carbon atoms or a group of the following formula

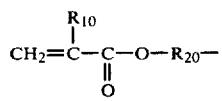

(wherein $R_{10}$ is hydrogen atom or methyl group; and $R_{20}$ is an alkylene group of from 2 to 10 carbon atoms, in which the number of carbon atoms in the main chain is 2 or more)

2. A polymerizable (and curable) composition comprised mainly of said melamine group-containing (meth)acrylate, a polymerization initiator, and if necessary, a polymerizable unsaturated group-containing monomer; and a molded article of a polymer obtained by the polymerization of said composition: and 3. A resin composition coated at least a part of its surface with a polymer of vinyl monomer comprised mainly of said malamine group-containing (meth)acrylate.

Figure 1:
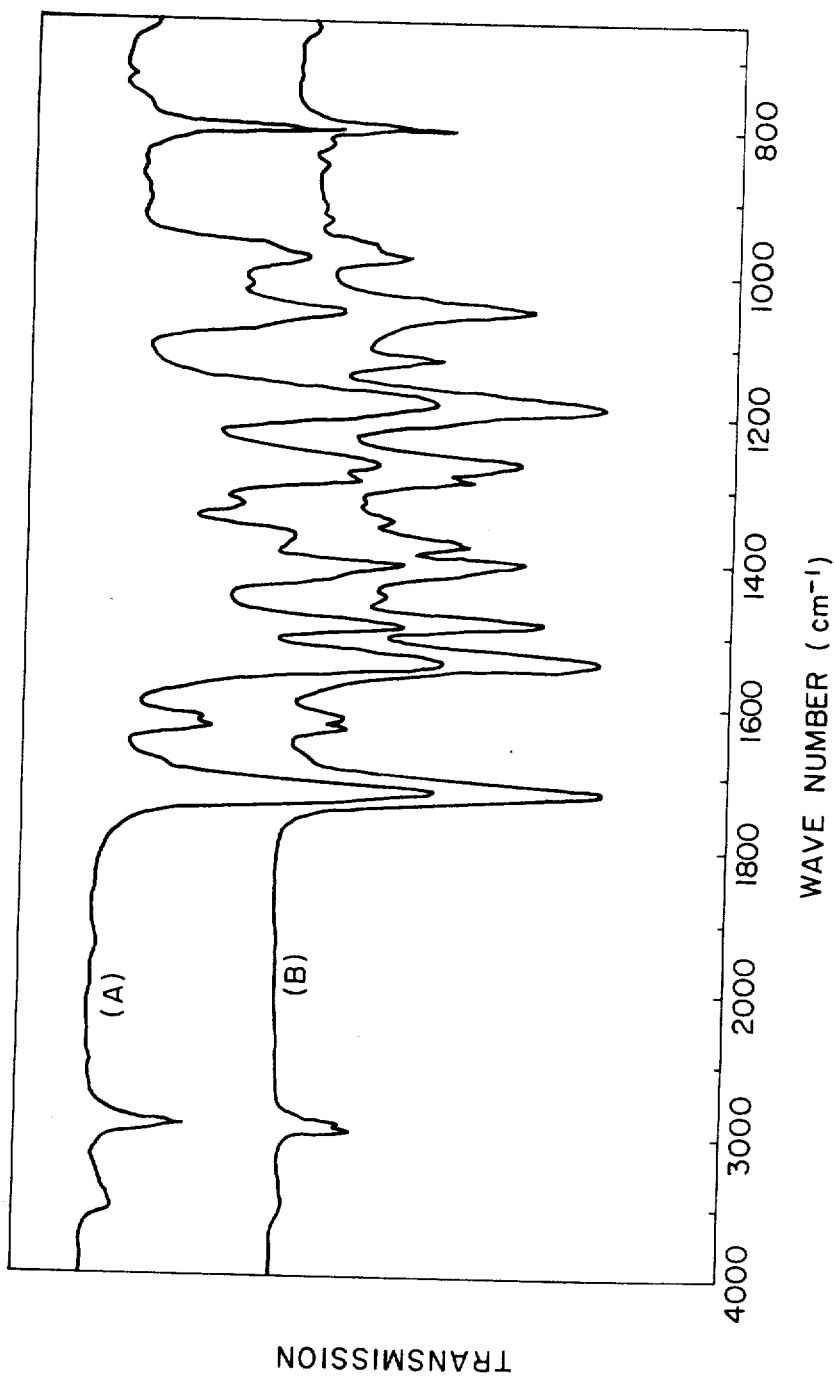
FIG. 1 is infrared absorption spector of melamine group-containing acrylates prepared by the method of Example 1 (curve (a)) and Example 2 (curve (b)).

The characteristics of the melamine group-containing (meth)acrylate of this invention having the aforesaid general formula (I) are exemplified as follows:

(1) The compound can be polymerized (and cured) by irradiating with light in the presence of a photopolymerization initiator, as well as by heating in the presence of, for example, a radical initiator, because of the existence of acrylic (or methacrylic) groups in the molecule; consequently, either of the above polymerization processes, including the low temperature polymerization process, can be selected according to the polymerization temperature requirement.

(2) The existence of 3 to 6 acrylic and (or) methacrylic groups in a molecule ensures a sufficiently high crosslink density similar to a melamine condensate.

(3) Because of its melamine skeleton and high crosslink density, the polymer obtained has high hardness, and, similar to the conventional melamine resin is especially useful as a laminating material and a coating material for the surface hardening of plastic, film, etc.

(4) The durability of a cured product is excellent because there is no methylol melamine-type active methylene structure in the molecule.

(5) The compound has excellent storage stability.

In the above general formula (I) which represents the melamine group-containing (meth)acrylate of the present invention; $R_{11}$, $R_{12}$ and $R_{13}$ are each same or different hydrogen atom or methyl group; $R_{21}$, $R_{22}$ and $R_{23}$ are each same or different a straight or branched chain alkylene group of from 2 to 10, preferably from 2 to 6, carbon atoms, in which the number of carbon atoms in the main chain is 2 or more, wherein the preferable examples of said alkylene group are

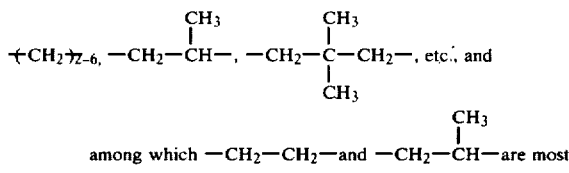

preferable in view of the availability of raw materials and the characteristics of the product; $R_{31}$, $R_{32}$ and $R_{33}$ are each same or different hydrogen atom, a hydrocarbon group of from 1 to 10 carbon atoms or a group of formula

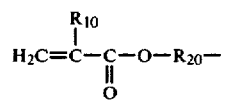

wherein $R_{10}$ is hydrogen atom or methyl group; and $R_{20}$ is an alkylene group of from 2 to 10, preferably from 2 to 6, carbon atoms, in which the number of carbon atoms in the main chain is 2 or more. Concrete examples of $R_{20}$ are the same as described in $R_{21}$-$R_{23}$.

Examples of the above hydrocarbon group are aliphatic, alicyclic or aromatic hydrocarbon groups of from 1 to 10, preferably from 1 to 8, carbon atoms. Suitable examples thereof are a straight or branched chain aliphatic hydrocarbon group such as methyl, ethyl, propyl, isopropyl, butyl, isobutyl, pentyl, neopentyl, hexyl, benzyl, etc., an alicyclic hydrocarbon group such as cyclopentyl, cyclohexyl, etc., and an aromatic hydrocarbon group such as phenyl, tolyl, etc. The above hydrocarbon group may have a substitution group such as halogen.

The melamine group-containing (meth)acrylate of the present invention is easily synthesized by reacting a melamine group-containing polyol obtained either by the dehydrochlorination reaction of a primary and/or secondary amine having a hydroxyl group with cyanuric chloride or by the addition reaction of melamine with an epoxy compound, with (meth)acrylic acid and/or its derivative, for example, (meth)acrylic anhydride, (meth)acryloyl chloride, (meth)acrylic esters, etc.

An example of the general synthetic procedures of the above melamine group-containing polyol is shown below: (An example of the synthesis of a melamine group-containing polyol)

1 Mole of cyanuric chloride is dissolved in about 400 ml of dioxane, and the solution thus obtained is slurrified by pouring into about 600 g of iced water under vigorous agitation. About 3 times mole of a hydroxyl-containing amine is added to the slurry while keeping the reaction temperature below about 40° C. by cooling the reaction system. Thereafter, the reaction temperature is slowly raised to the reflux temperature, and kept at that temperature for from 1 to 10 hours. During the heating and refluxing processes an aqueous solution containing about 3 times mole of sodium hydroxide was added dropwisely to the reaction system to maintain the system to a neutral or weak alkaline state. The reaction system is cooled, and the reaction product separated from the aqueous medium as crystals or oily substance, is washed with water and dried. According to circumstances, the dried product may be purified by recrystallization using a proper solvent.

The reaction of the melamine group-containing polyol with (meth)acrylic acid and/or its derivative (for example, (meth)acrylic anhydride, (meth)acryloyl chloride, (meth)acrylic ester, etc.) is usually carried out as follows:

(Direct Esterification Process)

A melamine group-containing polyol and about 1 to 2 equivalent, based on 1 equivalent of hydroxyl group of said polyol, of (meth)acrylic acid are dissolved in a solvent such as benzene, toluene, xylene, ethylene chloride, chlorobenzene, etc., and refluxed for from 1 to 20 hours in the presence of about 0.01 to 10 mole % of an acid catalyst such as cross-linked polystyrene having substitution groups of sulfuric acid, p-toluenesulfonic acid, phosphoric acid, or sulfonic acid residue. During the reflux, produced water is distilled off from the reaction system forming an azeotropic mixture with the solvent used, and the dehydration condensation reaction proceeds. The reaction mixture is washed successively with dilute alkaline aqueous solution and water, and the reaction solvent is distilled off to obtain the objective melamine group-containing (meth)acrylate.

(Ester Exchange Process)

A melamine group-containing polyol is made to react with large excess equivalent of a (meth)acrylic ester such as methyl (meth)acrylate, ethyl (meth)acrylate, etc. in the presence of about 0.01-10 mole % of an acid catalyst such as sulfuric acid, toluenesulfonic acid, tetrabutyl titanate, etc. or a basic catalyst such as sodium methoxide, by heating the reaction system above the boiling point of the (meth)acrylic ester used, whereby the produced lower alcohol is usually distilled off from the system forming an azeotropic mixture with the above (meth)acrylic ester, and the ester-exchange reaction proceeds. After the completion of the reaction, the catalyst in the reaction mixture is neutralized, the mixture is washed with water, and the above (meth)acrylic ester is distilled off from the mixture to obtain the objective melamine group-containing (meth)acrylate.

(Acid Halide Process)

A melamine group-containing polyol is made to react with about 1 to 1.5 equivalent, based on 1 equivalent of hydroxyl group of said polyol, of (meth)acryloyl halide in the presence of a deacidifying agent, usually in a solvent, at 0°–100° C. for 1–20 hours.

After the completion of the reaction, the reaction mixture is washed with water after or without removing the salt produced as a reaction by-product by filtering, and the solvent is distilled off from the mixture to obtain the objective melamine group-containing (meth)acrylate. Said deacidifying agent is usually an inorganic basic compound such as sodium hydrogen carbonate, sodium carbonate, potassium carbonate, sodium hydroxide, potassium hydroxide, etc. or a tertiary amine such as triethylamine, pyridine, N,N-dimethylaniline, etc.; and said solvent is usually an inert solvent such as benzene, toluene, chloroform, dioxane, tetrahydrofuran, ethyl acetate, etc.

(Acid Anhydride Process)

A melamine group-containing polyol is made to react with about 1–1.5 equivalent, based on 1 equivalent of hydroxyl group of said polyol, of (meth)acrylic anhydride at 0°–100° C. for 1–20 hours. The objective melamine group-containing (meth)acrylate is obtained by washing the reaction mixture with water and dilute alkaline aqueous solution, and when a solvent is used in the reaction, distilling the solvent off from the reaction mixture. The reaction can be conducted in a solvent, if desired. Examples of the solvent are (meth)acrylic acid, chloroform, benzene, ethyl acetate, dioxane, tetrahydrofuran, etc. Although the (meth)acrylate compound expressed by the formula (I) and obtained by the above procedures may be sometimes separated and purified by the conventional distillation, recrystallization, etc., it does not crystallize, in general, and is obtained as a high-boiling liquid substance. In such a case, the product can be purified by removing the unreacted raw materials and by-products from the reaction mixture by distillation, extraction, etc.

The compound (I) can be identified by means of infrared absorption spectrum, elemental analysis, nuclear magnetic resonance absorption spectrum, chromatography, mass spectrometry, iodine value, etc. Although various by-products may sometimes be produced depending upon the reaction conditions by the synthesis of the (meth)acrylate expressed by the general formula (I), the reaction mixture as produced can be used for the objects of the present invention provided that the total amount of the by-products is small compared with the objective product. Preferable concrete examples of the melamine group-containing (meth)acrylate of the present invention are given below: Hexakis[2-(meth)acryloyloxyethyl]melamine, hexakis[2-(meth)acryloyloxypropyl]melamine, hexakis[3-(meth)acryloyloxypropyl]melamine, hexakis[4-(meth)acryloyloxybutyl]melamine, hexakis[2-(meth)acryloyloxybutyl]melamine, hexakis[3-(meth)acryloyloxy-2-methylpropyl]melamine, hexakis[5-(meth)acryloyloxypentyl]melamine, hexakis[3-(meth)acryloyloxy-2,2-dimethylpropyl]melamine, hexakis[2-(meth)acryloyloxy-3-methylbutyl]melamine, hexakis[6-(meth)acryloyloxyhexyl]melamine, hexakis[2-(meth)acryloyloxy-4-ethylbutyl]melamine, $N^2,N^2,N^4,N^4,N^6$-pentakis(2-acryloyloxyethyl)-$N^6$-2-methacryloyloxyethylmelamine, $N^2,N^2,N^4,N^6$-tetrakis(2-acryloyloxyethyl)-$N^4,N^6$-bis(2-methacryloyloxyethyl)melamine, $N^2,N^4,N^6$-tris(2-acryloyloxypropyl)$N^2,N^4,N^6$-tris(2-methacryloyloxypropyl)melamine, $N^2,N^2,N^4$-tris(2-acryloyloxypropyl)-$N^4,N^6,N^6$-tris(2-methacryloyloxypropyl)melamine, $N^2,N^2,N^4,N^4,N^6$-pentakis(2-acryloyloxybutyl)-$N^6$-2-methacryloyloxybutylmelamine, $N^2,N^2,N^4,N^6$-tetrakis(4-methacryloyloxybutyl)-$N^4,N^6$-bis(4-acryloyloxybutyl)melamine, $N^2,N^4,N^6$-tris(6-methacryloyloxyhexyl)-$N^2,N^4,N^6$-tris(6-methacryloyloxyhexyl)melamine, $N^2,N^2,N^4,N^6$-tetrakis[2-acryloyloxyethyl]-$N^4,N^6$-bis[2-acryloyloxypropyl]melamine, $N^2,N^4,N^6$-tris[2-acryloyloxyethyl]-$N^2,N^4,N^6$-tris[4-methacryloyloxybutyl]melamine, $N^2,N^2,N^4,N^4$-tetrakis[2-(meth)acryloyloxyethyl]-$N^6,N^6$-bis[2-(meth)acryloyloxypropyl]melamine, $N^2,N^2,N^4,N^4$-tetrakis[2(meth)acryloyloxyethyl]-$N^6,N^6$-bis[2-(meth)acryloyloxybutyl]melamine, $N^2,N^2,N^4,N^4$-tetrakis[4-(meth)acryloyloxybutyl]-$N^6,N^6$-bis[2-(meth- )acryloyloxypropyl]melamine, $N^2,N^2$-bis[2-(meth)acryloyloxyethyl]-$N^4,N^4$-bis[2-(meth)acryloyloxypropyl]-$N^6,N^6$-bis[4-(meth)acryloyloxybutyl]melamine, $N^2,N^4,N^6$-tris[2-(meth)acryloyloxyethyl]-$N^2,N^4,N^6$-triethylmelamine, $N^2,N^4,N^6$-tris[2-(meth)acryloyloxypropyl]-$N^2,N^4,N^6$-tributylmelamine, $N^2,N^4,N^6$-tris[2-(meth)acryloyloxypropyl]$N^2$,,$N^4,N^6$-trihexylmelamine, $N^2,N^4,N^6$-tris[2-(meth)acryloyloxyethyl]-$N^2,N^4,N^6$-tricyclohexylmelamine, $N^2,N^4,N^6$-tris[2-(meth)acryloyloxyethyl]-$N^2,N^4,N^6$-tribenzylmelamine, $N^2,N^4,N^6$-tris[2-(meth)acryloyloxypropyl]-$N^2,N^4,N^6$-triphenylmelamine, $N^2,N^4,N^6$-tris[4-(meth)acryloyloxybutyl]-$N^2,N^4,N^6$-triethylmelamine, $N^2,N^4,N^6$-tris[4-(meth)acryloyloxybutyl]-$N^2,N^4,N^6$-triethylmelamine, $N^2,N^4,N^6$-tris[4-(meth)acryloyloxybutyl]-$N^2,N^4,N^6$-tribenzylmelamine, $N^2,N^4,N^6$-tris[6-(meth)acryloyloxyhexyl]melamine, $N^2,N^4,N^6$-tris[6-(meth)acryloyloxyhexyl]-$N^2,N^4,N^6$-tris(2-methylpropyl)melamine, $N^2,N^4,N^6$-tris[6-(meth)acryloyloxyhexyl]-$N^2,N^4,N^6$-tris(4-methylphenyl)melamine, $N^2,N^4$-bis(2-acryloyloxyethyl)-$N^6$-2-methacryloyloxyethyl-$N^2,N^4,N^6$-triethylmelamine, $N^2,N^4$-bis(2-methacryloyloxypropyl)-$N^6$-acryloyloxypropyl-$N^2,N^4,N^6$-tribenzylmelamine, $N^2,N^4$-bis(4-methacryloyloxybutyl)-$N^6$-4-acryloyloxybutyl-$N^2,N^4,N^6$-tricyclohexylmelamine, $N^2,N^4$-bis(6-acryloyloxyhexyl)-$N^6$-6-methacryloyloxyhexyl-$N^2,N^4,N^6$-trihexylmelamine, $N^2,N^4$-bis(3-acryloyloxy-2,2-dimethylpropyl)-$N^6$-(3-methacryloyloxy-2,2-dimethylpropyl)-$N^2,N^4,N^6$-triphenylmelamine, $N^2,N^4$-bis(3-acryloyloxy-2,2-dimethylpropyl)-$N^6$-(3-methacryloyloxy-2,2-dimethylpropyl)melamine, $N^2,N^4$-bis(2-acryloyloxyethyl)-$N^6$-2-acryloyloxypropyl-$N^2,N^4,N^6$-triethylmelamine, $N^2,N^4$-bis(2-acryloyloxyethyl)-$N^6$-2-methacryloyloxypropyl-$N^2,N^4$-diethyl-$N^6$-butylmelamine, $N^2,N^4$-bis[2-acryloyloxyethyl]-$N^6$-4-methacryloyloxybutyl-$N^2,N^4$-dibenzylmelamine, and $N^2$-2-acryloyloxyethyl-$N^4$-2-acryloyloxypropyl-$N^6$-2-methacryloyloxybutyl-$N^2,N^4,N^6$-triethylmelamine. Such melamine group-containing (methacrylate can be cured (polymerized) by various means according to its use. The curing may be carried out in the presence of a polymerization initiator. The types of the polymerization initiator differ with the curing method; in case of ultraviolet curing, the examples of preferable polymerization initiator are: benzophenone; benzoin ethers such as benzoin methyl ether and benzoin ethyl ether; benzyl; benzyl ketals such as benzyl dimethyl ketal, and benzyl diethyl ketal; 2-alkyl anthraquinones; and diacetyls; and in case of thermal curing, the examples of preferable polymerization initiator are; azo compounds such as azobisisobutyronitrile; and peroxides such as benzoyl peroxide, lauroyl peroxide, di-tert-butyl peroxide, dicumyl peroxide, and cumene hydroperoxide. The amount of such polymerization initiator is preferably between 0.01 and 10% by weight based on the melamine group-containing (meth)acrylate. In case of curing by gamma ray or electron beam irradiation, it is not always necessary to add a polymerization initiator to the reaction system. Description of methods for the curing of the compound will be given later.

The melamine grou-containing (meth)acrylate of the formula (I) can be used for various applications as a polyfunctional acrylate compound. Especially, because of its excellent characteristics mentioned above, the compound of the formula (I) can be used for a transparent resin molded article having high hardness, a surface treating agent, especially a coating agent for a thermoplastic resin, a reinforced resin molded article, or a component of paint, ink, adhesive, printing material, sealant, etc. Above all, it is most useful as a component of a transparent resin molded article, a surface treating agent and a reinforced resin molded article.

In the various modes of applications of the melamine group-containing (meth)acrylate of the general formula (I), the following description relates to those used as a cured resin molded article or reinforced resin molded article.

The molding is preferably carried out by mixing said melamine group-containing (meth)acrylate homogeneously with said polymerization initiator thereby dissolving the initiator to the (meth)acrylate, and molding and curing the resulting polymerizable (and curable) resin composition.

One of the methods for the preparation of said polymerizable (and curable) resin composition is to dissolve the polymerization initiator in a low-boiling solvent which is a good solvent of said (meth)acrylate and the polymerization initiator, for example, acetone, methyl ethyl ketone, chloroform, ethyl alcohol, tetrahydrofuran, dioxane, ethyl acetate and benzene, and thereafter dissolve said (meth)acrylate in the solution obtained above. After dissolution, the solvent may be removed, if necessary, by evaporation.

For the polymerizable (and curable) composition, a mixture of said melamine group-containing (meth)acrylate and a given amount of the polymerization initiator can be used as it is; and the composition may contain a conventional vinyl monomer having a polymerizable unsaturated group to decrease the viscosity, to control the rate of polymerization and the degree of crosslinking, or to improve various properties such as mechanical, chemical, physical, thermal or electrical properties. Examples of the vinyl monomer used for such objects are: vinyl chloride, vinylidene chloride, vinyl pyridine, N-vinyl pyrrolidone, styrene, methyl methacrylate, acrylonitrile, acrylic acid, vinyl acetate, methacrylamide, 2-hydroxyethyl acrylate, tetrahydrofurfuryl methacrylate, 2-ethylhexyl methacrylate, tetramethylene glycol dimethacrylate, polyethyleneglycol dimethacrylate, trimethylolpropane triacrylate, pentaerythrytol tetramethacrylate, diallyl carbonate, diallyl phthalate, and n-butyl allyl ether. The amount of the monomer is preferably less than 40% by weight, more preferably less than 30% by weight, based on the polymerizable (and curable) composition obtained. The monomer may be used either solely or by mixing two or more monomers.

A storage stabilizer is not always necessary to be added to the polymerizable (and curable) composition thus obtained; however, a thermal polymerization inhibitor is usually effective for such purpose. The examples of such thermal polymerization inhibitor are: hydroquinone, hydroquinone monomethyl ether, catechol, 2,6-di-t-butylphenol, benzoquinone, N-nitrosodiphenylamine, and phenothiazine. In case of using such thermal polymerization inhibitor, its amount is preferably from 10 to 10000 ppm based on the polymerizable (and curable) composition. Other additives, for example, stabilizers, such as ultraviolet absorbing agent, antioxidant, etc., dyes and pigments, fluorescent dyes and pigments, and fillers such as glass fiber, glass powder, clay, carbon fiber, etc., may be added to the composition.

Although the means for the curing of the polymerizable (and curable) composition of this invention differ with the kind of the polymerization initiator used, a thermal and/or photo polymerization process is preferably used. In case of the photo-polymerization, irradiation with light ranging between ultraviolet ray and visible light is especially preferable.

Any heat sources can be used for the thermal polymerization, however, heat sources such as oven, hot plate, hot mold, heating medium, hot air, infrared ray, microwave, and ultrasonic wave are preferably referred.

The light source is usually a carbon-arc lamp, a super high pressure mercury-vapor lamp, high pressure mercury vapor lamp, low pressure mercury vapor lamp, xenon lamp, chemical lamp, and halogen lamp.

The curing of the polymerizable (and curable) composition is carried out by the above means in this invention. The curing conditions are usually those given below:

The curing conditions of the polymerizable (and curable) composition for manufacturing an article having a thickness of the order of mm such as the one obtained by a conventional molding process will be discussed first, while leaving those for the preparation of a thin-film cured product such as coating, printing ink, paint, etc., later.

In the case of the curing of a thick-walled product, it is important to conduct the polymerization (and curing) process slowly, allowing plenty of time therefor, because rapid curing may cause internal defects in the cured article such as mechanical strain, optical strain, internal cracking and void, due to the heat generation and the volume shrinkage by polymerization (and curing).

Although the time and temperature of the thermal curing process cannot be defined indiscriminately because of their dependency upon the curing conditions as well as the shape, size and use of the cured product and the molding method, they are usually in the ranges between about 50° C. and 150° C., and between about 30 minutes and several days, respectively.

In the case of photo-curing, the intensity of light having wavelengths effective to the polymerization (and curing) decreases gradually from the surface to the inner part of the article to be cured, and the thickness of the article is restricted to about 5 mm to assure sufficient light irradiation. The curing time is usually between several tens seconds and about 30 minutes, depending upon the type and intensity of the light source, distance from the light source, and shape, thickness and use of the cured article. The photo-curing process is especially suitable for the curing of a flat, transparent, and/or thin-walled article. The photo-polymerization (and curing) can be carried out even at room temperature.

The polymerization (and curable) composition can be molded by known molding processes such as casting, injection molding, compression molding, transfer molding, sintering, etc. The physical properties, such as percentage composition and viscosity, of the polymerizable (and curable) composition are preferably selected to meet with the molding process and the desired characteristics of the molded article, which can easily be determined and practiced by a person with ordinary skill in the art.

Examples of the molded article of the polymer thus obtained are: film or plate such as film, foil, sheet, board, etc.; fibrous material such as fiber, filament, etc.; tubular products such as tube; and various other molded products such as miniature casing, e.g. transistor case, etc., plug cap, connector, switch, distributor, computer parts, tableware, gas appliance parts, controlling device, lens, cabinet, and valve.

Because of the excellent physical properties such as hardness, heat resistance, electrical insulation, etc., of the cured product, the polymerizable (and curable) composition of this invention can be used to a wide variety of uses such as a coating agent for imparting abrasion resistance, electrical insulation, heat resistance, etc. to a molded article a molded article such as a display, various laminates having a substrate, e.g. paper, asbestos paper, cotton cloth, glass woven cloth, etc., an organic glass, eyeglasses, etc.; and other materials such as paint, ink, printing material, sealant, etc.

The following description relates to the applications of the melamine group-containing (meth)acrylate of the general formla (I) as a plastic coating agent. The characteristic features of a molded article coated at least a part of the surface thereof with a polymer of a vinyl monomer composition composed mainly of said melamine group-containing (meth)acrylate, and those of the process for the preparation of said molded article, are described as follows:

(1) A high surface hardness of the coating layer can be attained by the formation of higher order network structure attributable to the polyfunctional nature of the polymer of the (meth) acrylate compound. In spite of the higher order network structure, a so-called star-like structure of the monomer with a bulky heterocyclic ring at its center, results in low shrinkage by polymerization. Accordingly, the dimensional stability of the polymer is high, and the curling phenomenon, which sometimes occurs in the case of coating a thin film or a sheet, can be minimized.

(2) Since the coating is an organic material, it has high flexibility, and endures severe deformations such as binding and elongation which occasionally occur in a coated thin film, without cracking.

(3) The coating material has high affinity, and accordingly high adhesivity to the substrate, supposedly due to the dipole-dipole interaction between the coating material whose main component being (meth)acrylate compound, and the ester bond of the substrate such as polyester, polycarbonate, polydialkylene-glycol bis(allyl carbonate), etc., and an interaction originated from the dispersion force between the aromatic heterocyclic group of the coating material and the substrate.

(4) The use of radical reaction ensures a rapid reaction and low-temperature polymerization (and curing), which facilitates the continuous coating operation and is especially advantageous for the processing of continuous lengths. On the contrary, conventional condensation coating compositions represented by organosiloxane and polysilicic acid are slow to react, and necessary to be treated at a high temperature for a long time. Such a treatment is unfavorable for the coating of continuous lengths. Some attempts have been made to attain the low-temperature, short-time treatment by the addition of acidic, basic or metallic catalysts; however, the use of such catalyst may cause the lowering of other physical properties or durability. Furthermore, the coating by vacuum deposition also necessitates a long time to obtain a layer having a sufficient thickness to impart high abrasion resistance, and is not economical.

(5) As the coating composition contains a (meth)acrylate compound, it can be cured by heat polymerization in the presence of a radical initiator, or by photo-polymerization in the presence of a photo-sensitizer, or by ionizing radiation-induced polymerization. Furthermore, the curing of the above composition is extremely advantageous because the (meth)acrylate compound is polyfunctional and the composition is, in most cases, curable in air.

(6) Since the melamine group-containing (meth)acrylate of this invention is devoid of a methylol melamine-type active methylene group, the composition is remarkably excellent in durabilities, especially water resistance and moisture resistance.

In case of using the melamine group-containing (meth)acrylate of the present invention expressed by the above general formula (I) as a coating agent for plastics, the coating agent contains at least one compound selected from the melamine group-containing (meth)acrylate expressed by the above general formula (I), and if necessary, a polymerization initiator, a polymerization inhibitor as a storage stabilizer, and various other additives, and furthermore, may be diluted with a proper organic solvent.

The solvent is effective to modify the viscosity of the agent or to improve the wettability of the agent to the article to be coated. Concrete examples of the solvent are as follows: Hydrocarbons such as benzene, toluene, xylene, ethylbenzene, n-hexane, heptane, petroleum ether, ligroin, cyclohexane, and methylcyclohexane; halogenated hydrocarbons such as methylene chloride, chloroform, trichlene, ethylene dichloride, perclene, 1,1,1-trichloroethane, 1,1,2,2-tetrachloroethane, propylene dichloride, chlorobenzene, bromoethane, and bromoform; alcohols such as methanol, ethanol, isopropyl, n-butanol, sec-butanol, amyl alcohol, methylamyl alcohol, cyclohexanol, ethylene glycol, trimethylene glycol, propylene glycol, glycerin, ethylene glycol monomethyl ether, ethylene glycol monoethyl ether, and diethylene glycol monomethyl ether; ketones such as acetone, methyl ethyl ketone, methyl isobutyl ketone, and cyclohexanone; ethers such as ethyl ether, propyl ether, butyl ethyl ether, isoamyl ether, diethylene glycol dimethyl ether, triethylene glycol dimethyl ether, tetrahydrofuran, dioxane, anisole, and phenetole; nitriles such as acetonitrile, propionitrile, and capronitrile; esters such as methyl formate, ethyl formate, methyl acetate, ethyl acetate, propyl acetate, isobutyl acetate, amyl acetate, methyl benzoate, and ethyl benzoate; aprotic polar solvents such as N,N-dimethyl formamide, N,N-dimethyl acetamide, N-methyl pyrrolidone, and dimethyl sulfoxide; and water. The above solvent can be used singly or by mixing two or more solvents.

The type of usable polymerization initiator differs with the means of curing, and its concrete examples are the same as those shown in the description of the polymerizable (and curable) compositions. As to the concrete examples of storage stabilizers, the situation is similar to the above. Further, the amounts of the polymerization initiator and the storage stabilizer are also same as those given in the above description.

Various other additives which may be added to the coating agent are, for example, a stabilizer such as an ultraviolet absorber and an antioxidant, a dye and/or pigment, a fluorescent dye and/or pigment, and a filler such as glass fiber, glass powder, clay, magnetic powder, and carbon, provided that the addition answers for the purpose of coating.

Further, said coating liquid may contain conventional vinyl monomer, provided that said vinyl monomer has no detrimental effect to the excellent abrasion resistance and adhesivity which are characteristic to the cured product of the melamine group-containing (meth)acrylic acid ester expressed by the above general formula (I). The examples and amount of the vinyl monomer are similar to those shown in the description of the polymerizable (and curable) composition.

The application (coating) of said coating liquid to a part or the whole surface of a substrate can be carried out by any of the following processes; dipping of substrate into the coating liquid, spraying to the substrate, coating by means of a brush, a doctor knife, a bar coater or a roll, and kiss roll coating. Any of these processes is satisfactory.

Said substrate may be pre-treated for the further improvement of adhesivity. Examples of such pre-treatments are; corona discharge treatment, plasma treatment, glow discharge treatment, flame treatment, ultraviolet or electron beam irradiation, ozone oxidation treatment and hydrolysis, and coating with an adhesive layer. The surface treatment is preferably applied to a polyester molded article.

When the coating liquid is diluted with a solvent, the solvent must be removed by heating the molded article coated with said coating liquid, or by other means; and when it does not contain solvent, it can be polymerized (and cured) without any treatment. The polymerization (and curing) can be carried out by ultraviolet irradiation, heating, gamma-ray irradiation, electron beam irradiation, or their combination; wherein ultraviolet irradiation, heating or their combination is preferable. Since most of the (meth)acrylate expressed by the above general formula (I) are curable in air (not inhibited by oxygen in air), it is usually unnecessary to carry out the polymerization in an inert atmosphere such as nitrogen gas, or under reduced pressure, or by shielding the reaction system from air with film or glass plate.

Curing of the coating liquid applied to a substrate is performed on the substrate.

Light sources used for the curing by ultraviolet irradiation are, for example, a carbon-arc lamp, a low pressure mercury vapor lamp, a high pressure mercury vapor lamp, a super high pressure mercury vapor lamp, a xenon lamp, a halogen lamp, and a chemical lamp. Time necessary for the ultraviolet curing can not be determined indiscriminately because of its dependency upon the type and intensity of the light source, distance between the light source and the object to be irradiated, and the atmosphere of irradiation; however, a short irradiation, for example, irradiation of the order of second (several to seconds), is sometimes sufficient to attain complete curing. The curing can be conducted at room temperature or in an atmosphere heated to an extent not to cause the heat deformation of the substrate.

Heat sources used for the curing by heating are, for example, an oven, a hot plate, hot air, infrared irradiation and microwave irradiation. Time necessary for the heat curing depends strongly upon the curing temperature; and it is usually several minutes to 5 minutes or more at temperatures above 80° C., preferably above 120° C. Therefore, the heat curing process is inadequate to the substrate having porr heat resistance, such as polyvinyl chloride and polyethylene. Although the heat curing process can successfully applied to a substrate having high heat resistance, such as an aromatic polyester and polycarbonate, it is preferably conducted in an inert gas atmosphere such as nitrogen gas or carbon dioxide gas, or by shielding the coating liquid from air (especially oxygen), in order to attain high abrasion resistance.

The ionizing radiation for curing is, usually, gamma ray radiated from a radioactive isotope such as Co⁶⁰, or electron beam generated by a 20 to 2,000 KV electron beam accelerator. The radiation curing can be usually carried out by irradiating in an inert gas atmosphere such as nitrogen or carbon dioxide to a total absorbed dose of from 0.5 to 50 Mrad. Since the radiation curing proceeds even at a low temperature, it is adequately applied even to a substance having poor heat resistance.

Among these curing processes, the ultraviolet curing is most preferable in view of the practicality and workability.

In the present invention, the substrates (molded articles) suitable to be coated with said coating liquid are those made of polyester, polycarbonate, polydialkylene glycol bis(allyl carbonate), etc.

Although there is no particular restriction on the type of the polyester, it is especially effective to apply the coating liquid of this invention to a polyester having rather poor adhesivity, such as a polyester wherein more than 85 mole % of the recurring units are an aromatic dicarboxylic acid and an aliphatic diol, because the cured product of the coating liquid of this invention exhibits excellent adhesivity even to the above poorly adhesive polyester.

The aromatic dicarboxylic acid is, for example, terephthalic acid, isophthalic acid, 4,4-diphenyl dicarboxylic acid, and 2,6-naphthalene dicarboxylic acid; and among them, terephthalic acid and 2,6-naphthalene dicarboxylic acid are more preferable.

The dicarboxylic acid component may contain less than 15 mole % of other dicarboxylic acid such as succinic acid, adipic acid, sebacic acid and hexahydroterephthalic acid, or an hydroxycarboxylic acid such as ε-hydroxycaproic acid and hydroxybenzoic acid. The diol component of the polyester is aliphatic diols such as ethylene glycol, trimethylene glycol, tetramethylene glycol, hexamethylene glycol and cyclohexane dimethanol; and among them, ethylene glycol and tetramethylene glycol are particularly preferable.

Among the polyesters cited above, polyethylene terephthalate and polybutylene terephthalate are particularly preferable.

Although there is no particular restriction on the type of the polycarbonate, a polycarbonate wherein more than 85 mole % of the recuring units are an aromatic diol carbonate is preferable. Examples of the preferable aromatic diol are: bisphenols such as bisphenol-A, bisphenol-F, bisphenol-Z,

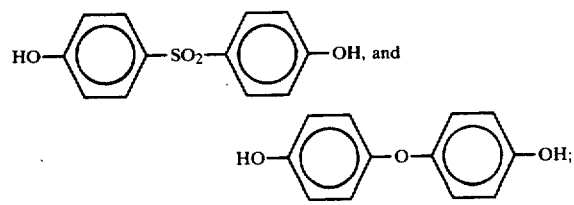

nucleus-substituted bisphenols such as

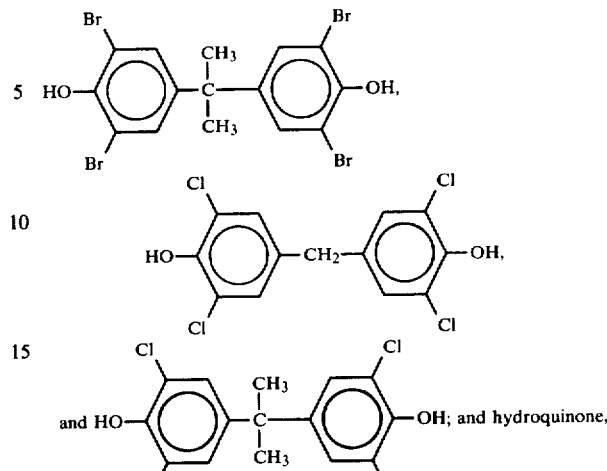

resorcinol, etc.

Among these polycarbonates, the most preferable is the one derived from bisphenol-A.

The dialkylene glycol bis(allyl carbonate), which is a main monomer of polydialkylene glycol bis(allyl carbonate), is expressed by the general formula given below:

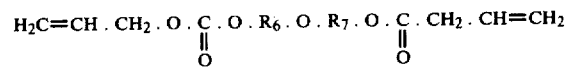

wherein $R_6$ and $R_7$ are the same or different straight or branched chain alkylene group of from 1 to 7, preferably from 2 to 5, carbon atoms. Preferable examples of the alkylene group are straight chain alkylene groups such as $-(CH_2)_{2-5}-$ and branched chain alkylene groups such as

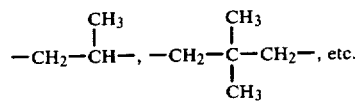

More preferably, both $R_6$ and $R_7$ are ethylene group.

A molded article of a resin other than the above-mentioned polyester, polycarbonate and polydialkylene glycol bis(allyl carbonate) can be used as the substrate of the present invention. Examples of such resin are: vinyl chloride resin; styrene resin such as polystyrene, acrylonitrile-styrene copolymer (AS resin), acrylonitrile-butadiene-styrene copolymer (ABS resin), etc.; methacrylate resin such as polymethyl methacrylate, methyl methacrylate copolymer, etc., cellulosic resin such as cellulose acetate; polyethylene; and polypropylene. There is no particular restriction on the form of the resin molded article and any form which has been conventionally used answers the purpose of this invention; however, in case of polyester or polycarbonate, film, sheet and plastic forms are preferable, whereas in case of polydialkylene glycol bis(allyl carbonate), plastic form is preferable. Since the coated article of this invention thus obtained has excellent surface properties, especially high abrasion resistance, and moreover, extremely high adhesivity between the coating layer and the substrate, the coating layer never peels off even under severe service conditions such as bending and folding. Therefore, the coated article of this invention can be applied to a wide variety of uses as an abrasion-resistant film, sheet or plastic. Concrete examples of the application are; eyeglasses, goggles, lens, windowpane, glass, windshield of airplane and automobile, curve mirror, showcase; electrical parts such as dust cover of a record player, front glass of a TV-set, cover of various instruments, etc.; door, baseboard, parapet, side board of an escalator, case of unit goods, etc.

The invention will be illustrated more specifically by the following Examples, which, however, do not restrict the scope of this invention.

All "parts" in the Examples are by weight.

The nuclear magnetic resonance absorption spectrum is measured at 60 MHz or 100 MHz using deutero chloroform ($CDCl_3$) as solvent.

EXAMPLE 1

A mixture consisting of 184.4 parts of cyanuric chloride and 413 parts of dioxane was poured into 600 parts of iced water under vigorous agitation to obtain a slurry. 316.2 Parts of diethanolamine was added dropwise to the slurry keeping the temperature of the reaction system below 30° C. by external cooling. A few drops of phenolphthalein solution was added to the reaction system, which was slowly heated to a reflux temperature and refluxed for 2 hours. During the heating and refluxing processes, a solution consisting of 120 parts of sodium hydroxide and 300 parts of water was added dropwise to the system while taking care not to cause coloring of phenolphthalein. Thereafter, the reaction system was cooled, solvents were removed therefrom, and the residue was dried. The residue was extracted with n-butanol and recrystallized from the solution, and 240 parts of acicular crystal of hexakis(2-hydroxyethyl)melamine was obtained.

39.1 Parts of the hexakis(2-hydroxyethyl)melamine obtained above was dissolved in 100 parts of acrylic acid together with 0.03 part of p-methoxy phenol; and 80 parts of acrylic acid anhydride was added dropwise to the solution at room temperature under agitation, and made to react at 40°-50° C. for 5 hours. The reaction product was added to 1200 parts of water under vigorous agitation, and thereafter, an organic layer was separated. 200 Parts of ethyl acetate was added to the organic layer, the mixture was washed twice with aqueous solution of sodium carbonate and three times with water. The organic phase was separated, added with 30 parts of magnesium sulfate, and dried. Solvents were removed therefrom by distillation leaving hexakis(2-acryloyloxyethyl)melamine as viscous liquid.

Figure 2:
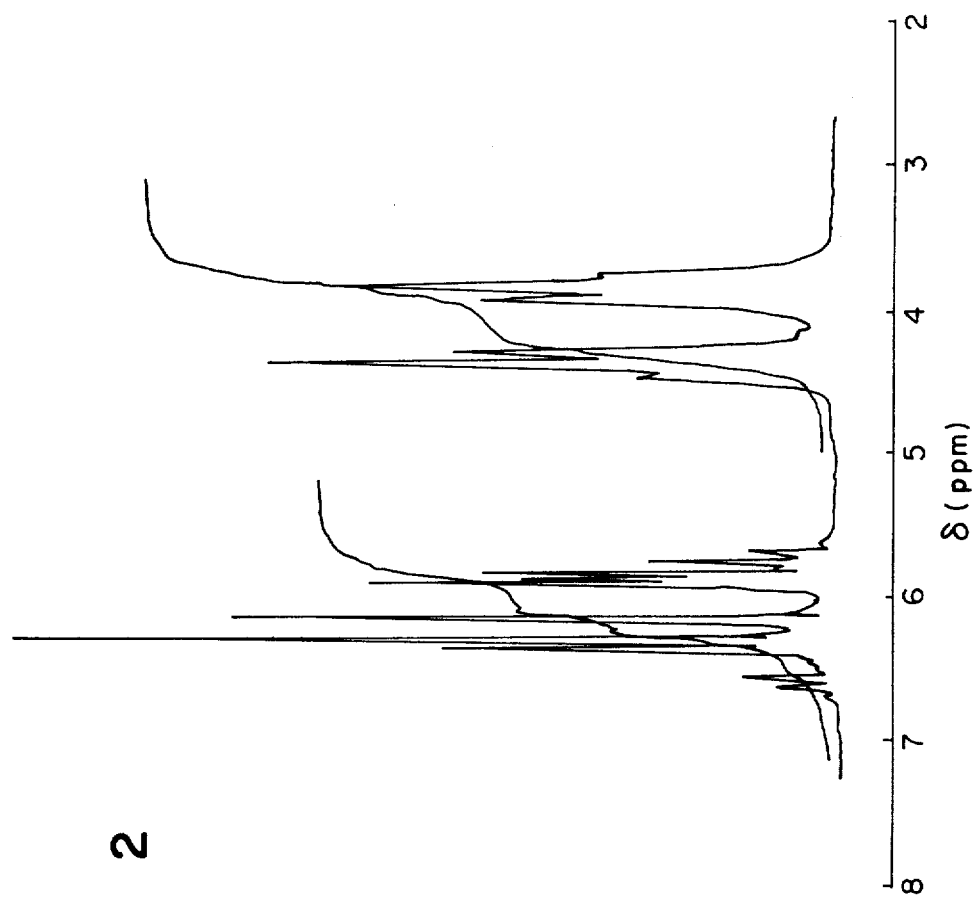
FIG. 2 is a nuclear magnetic resonance absorption spectrum of a melamine group-containing acrylate prepared by the method of Example 1.

The infrared absorption spectrum of the substance thus obtained is given in the FIG. 1 as the curve (a), which shows characteristic absorptions of ester group (1730 cm$^{-1}$), C=C group (1620 and 1635 cm$^{-1}$), and melamine (1540, 1490, and 805 cm$^{-1}$). The nuclear magnetic resonance absorption spectrum is given in the FIG. 2, which shows characteristic absorptions of $CH_2$—$CH_2$ (3.8 ppm: triplet, and 4.4 ppm: triplet) and $CH_2$=CH (5.7–6.7 ppm.)

The values of elemental analysis are shown below, which agree well with the calculated values.

|  | C | H | N |
|---|---|---|---|
| Analytical value (%) | 55.13 | 5.89 | 12.01 |
| Calculated value (%) | 55.45 | 5.92 | 11.76 |

EXAMPLE 2

300 Parts of hexakis(2-hydroxypropyl)melamine was prepared by a method similar to the Example 1, with the exception of using 400 parts of diisopropanolamine in place of 316.2 parts of diethanolamine.

47.5 Parts of the hexakis(2-hydroxypropyl)melamine obtained above was added to 83 parts of acrylic acid anhydride containing 0.03 part of p-methoxy phenol under agitation at room temperature, and the mixture was heated at 40°-50° C. for 6 hours. The reaction system was converted from slurry to a homogeneous solution by the heat treatment. The reaction product thus obtained was added to 800 parts of water under vigorous agitation, and organic layer was separated. By treating the organic layer in the same manner as the Example 1, 71 parts of hexakis(2-acryloyloxypropyl)melamine was obtained as viscous liquid.

The infrared absorption spectrum of the substance thus obtained is given in the FIG. 1 as the curve (b), which shows a characteristic absorptions of ester group (1730 cm$^{-1}$), C=C group (1620 and 1640 cm$^{-1}$), and melamine (1540, 1490, and 805 cm$^{-1}$).

Figure 3:
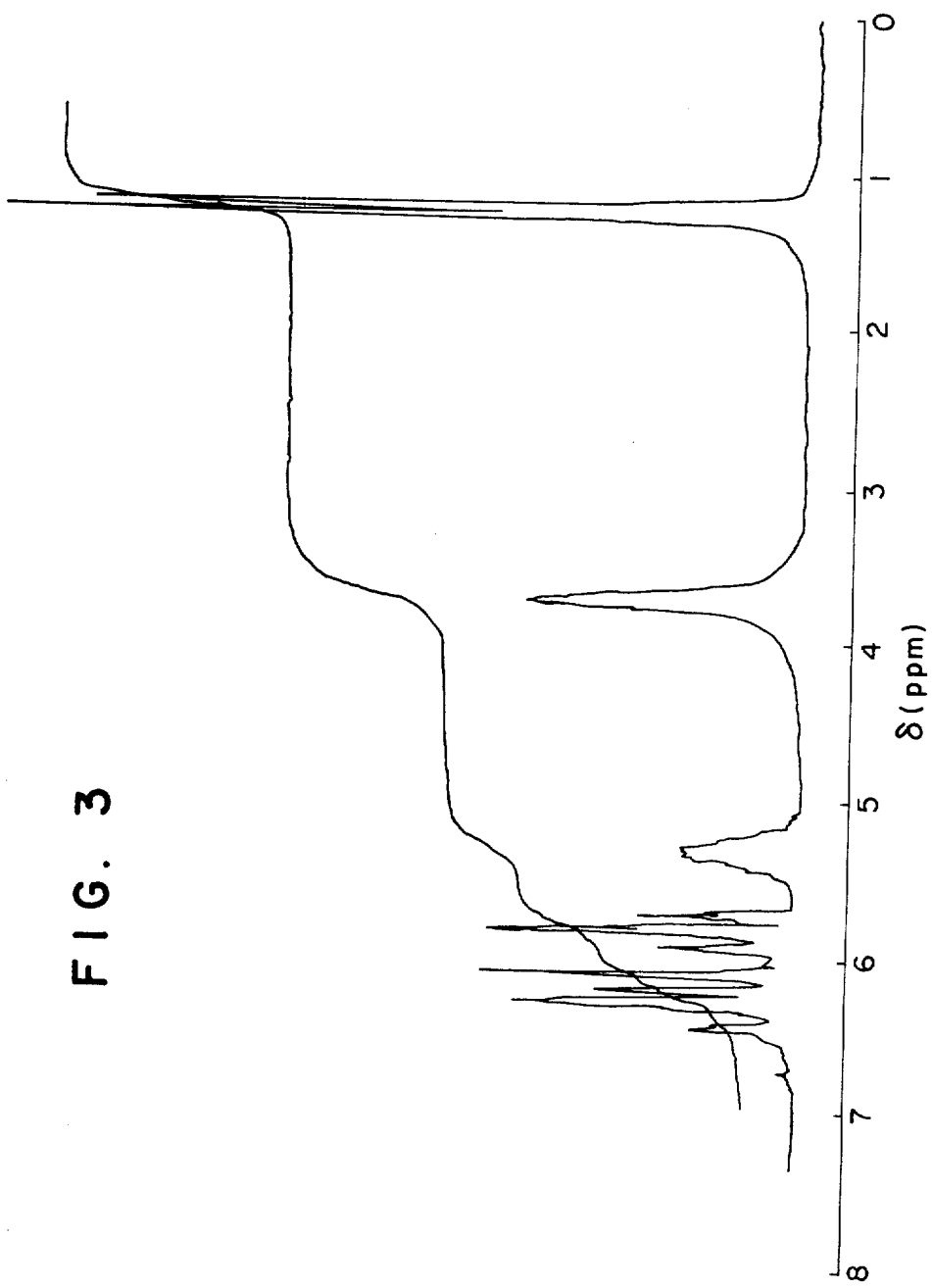
FIG. 3 is a nuclear magnetic resonance absorption spectrum of a melamine group-containing acrylate prepared by the method of Example 2.

The nuclear magnetic resonance absorption spectrum is given in the FIG. 3, which shows characteristic absorptions of

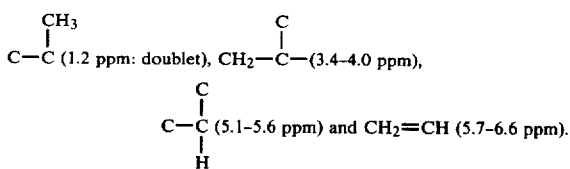

The values of elemental analysis are shown below, which agree well with the calculated values.

|  | C | H | N |
|---|---|---|---|
| Analytical value (%) | 70.14 | 7.48 | 10.51 |
| Calculated value (%) | 70.56 | 7.40 | 10.29 |

EXAMPLE 3

430 Parts of a melamine group-containing polyol of the formula

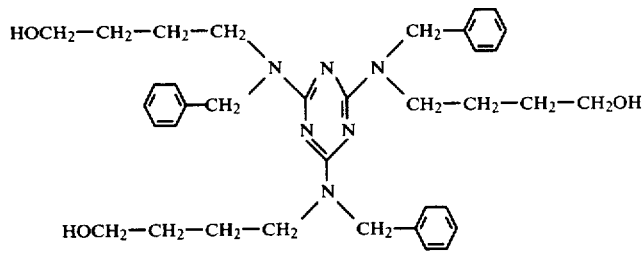

was prepared by a method similar to the Example 1 with the exception of using 537.8 parts of N-benzyl-4-butanolamine in place of diethanolamine.

61.3 Parts of the polyol obtained above and 0.03 part of hydroquinone were dissolved in 200 parts of dioxane, and the mixture was slurrified by adding 21.2 parts of finely divided sodium carbonate. 34.8 Parts of methacryloyl chloride was added dropwise to the slurry at room temperature under agitation, and made to react by heating at 50° C. for 2 hours. The reaction product was thrown into 1000 parts of water under vigorous agitation, and an organic layer was separated. The organic layer was treated in the same manner as the Example 1, and 75 parts of a melamine group-containing methacrylate of the aforesaid formula (I) (wherein $R_{11}$, $R_{12}$ and $R_{13}$ are —$CH_3$; $R_{21}$, $R_{22}$ and $R_{23}$ are —$CH_2.CH_2.CH_2.CH_2$; $R_{31}$, $R_{32}$ and $R_{33}$ are

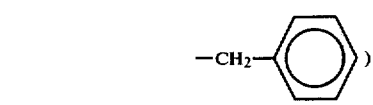

was obtained as viscous liquid.

Figure 4:
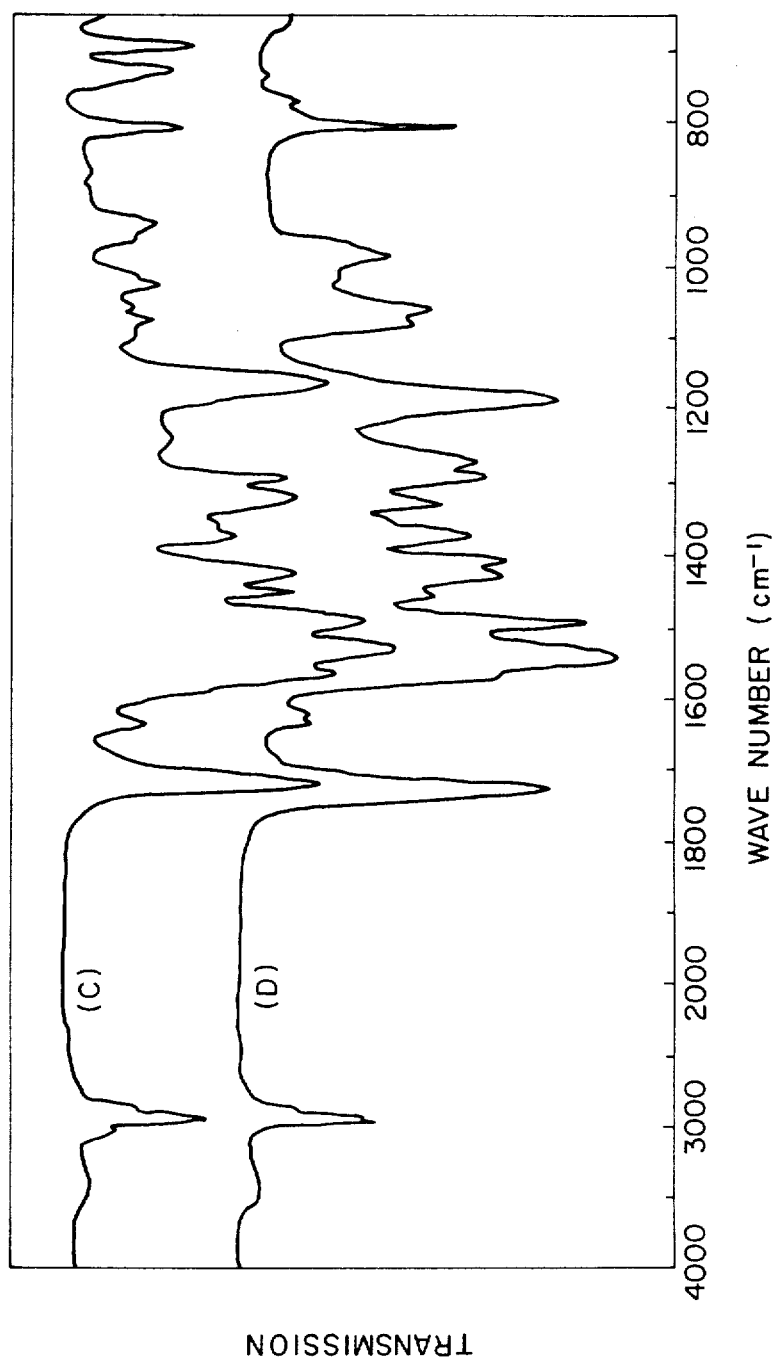
FIG. 4 is infrared absorption spectra of melamine group-containing methacrylate and acrylate prepared by the methods of Example 3 (curve (c)) and Example 5 (curve (d)), respectively.

The infrared absorption spectrum of the substance thus obtained is given in the FIG. 4 as the curve (C), which shows characteristic absorptions of ester group (1720 cm$^{-1}$), C=C group (1635 cm$^{-1}$), melamine group (1560, 1530, 1490, and 805 cm$^{-1}$), and C—H group (about 2950 cm$^{-1}$). The nuclear magnetic absorption spectrum shows characteristic absorptions of C—$CH_2$—$CH_2$—C (1.0-2.1 ppm), methyl group of methacrylate (1.9 ppm), N—$CH_2$—C (3.2-3.7 ppm), C—$CH_2$—O (3.7-4.3 ppm), methylene group of benzyl (4.75 ppm), $CH_2$=C (5.5 and 6.05 ppm) and phenyl group of benzyl (7.25 ppm); and the areal ratios of the above absorption peaks are 4:3:2:2:2:2(1+1):5.

The values of elemental analysis are shown below, which agree well with the calculated values.

|  | C | H | N |
|---|---|---|---|
| Analytical value (%) | 58.97 | 6.78 | 10.27 |
| Calculated value (%) | 58.63 | 6.81 | 10.52 |

EXAMPLE 4

280 Parts of a melamine group-containing polyol of the formula

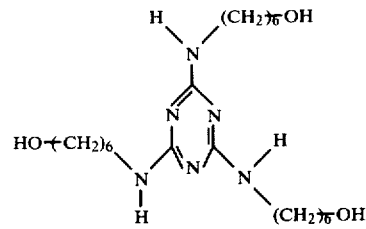

was prepared by a method similar to the Example 1 with the exception of using 351.6 parts of 6-hexanolamine in place of diethanolamine.

Using 42.7 parts of the melamine group-containing polyol obtained above, 0.03 part of p-methoxy phenol and 40 parts of acrylic anhydride as raw materials, 54 parts of a melamine group-containing acrylate of the general formula (I) (wherein $R_{11}$, $R_{12}$ and $R_{13}$ are H; $R_{21}$, $R_{22}$ and $R_{23}$ are $CH_2.CH_2.CH_2.CH_2.CH_2.CH_2$; $R_{31}$, $R_{32}$ and $R_{33}$ are H) was obtained as viscous liquid by the process similar to the Example 2.

Figure 5:
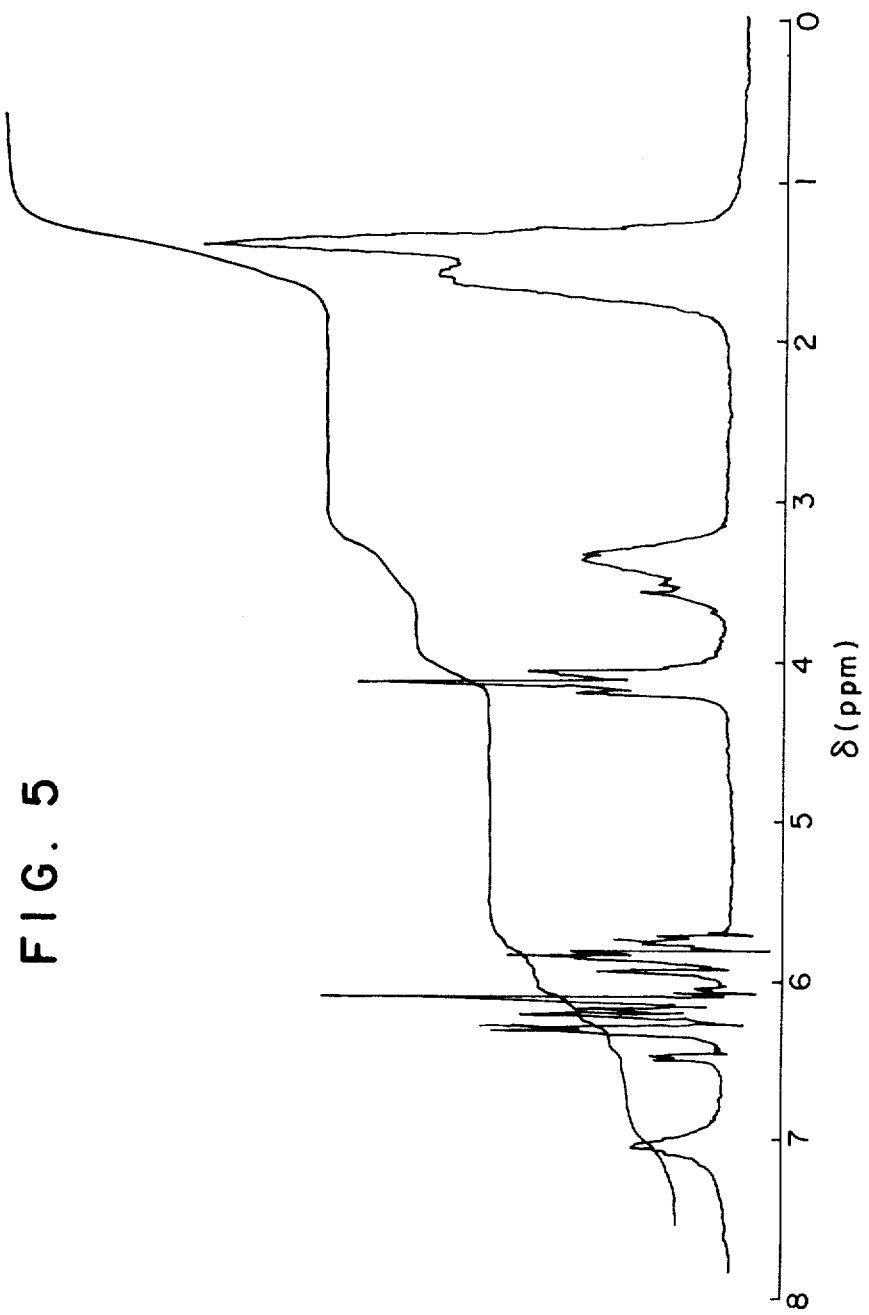
FIG. 5 is a nuclear magnetic resonance absorption spectrum of a melamine group-containing acrylate prepared by the method of Example 4.

The infrared absorption spectrum shows characteristic absorptions of ester group (1730 cm$^{-1}$), $CH_2$=CH group (1615 and 1630 (shoulder) cm$^{-1}$), melamine (1570, 1510 and 810 cm$^{-1}$), methylene group (2850 and 2950 cm$^{-1}$) and N-H group (3300-3400 cm$^{-1}$). The nuclear magnetic absorption spectrum given in the FIG. 5 shows characteristic absorptions of C—$CH_2$—$CH_2$—$CH_2$—$CH_2$—C (1.1-2.0 ppm), N—$CH_2$—C (3.1-3.8 ppm), C—$CH_2$—O (3.9-4.3 ppm), $CH_2$=C (5.7-6.5 ppm) and N-H (6.8-7.2 ppm).

The values of elemental analysis are shown below, which agree well with the calculated values.

|  | C | H | N |
|---|---|---|---|
| Analytical value (%) | 61.12 | 8.15 | 14.50 |
| Calculated value (%) | 61.20 | 8.22 | 14.28 |

EXAMPLE 5

270 Parts of a melamine group-containing polyol of the formula

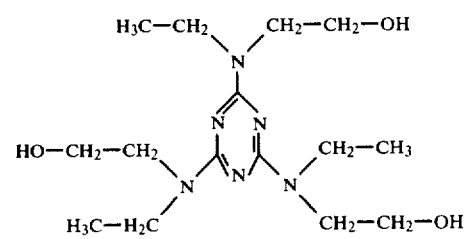

was prepared by a method similar to the Example 1 with the exception of using 267.4 parts of N-ethylethanolamine in place of diethanolamine.

Using 34.2 parts of the melamine group-containing polyol obtained above, 0.02 part of p-methoxy phenol, 50 parts of acrylic acid and 40 parts of acrylic anhydride as raw materials, 48 parts of a melamine group-containing acrylate of the general formula (I) (wherein $R_{11}$, $R_{12}$, and $R_{13}$ are H; $R_{21}$, $R_{22}$ and $R_{23}$ are $CH_2.CH_2$; $R_{31}$, $R_{32}$ and $R_{33}$ are $CH_3.CH_2$) was obtained as viscous liquid by the process similar to the Example 1.

The infrared spectrum of the substance thus obtained is given in FIG. 4 as a curve (d), which shows characteristic absorptions of ester (1730 cm$^{-1}$), $CH_2$=CH (1620 and 1630 cm$^{-1}$), melamine (1540, 1490 and 810 cm$^{-1}$), and C—H (2950 (shoulder) and 2980 cm$^{-1}$). The nuclear magnetic absorption spectrum shows characteristic absorptions of terminal methyl or ethyl group (1.15 ppm; triplet),

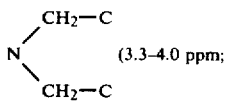
(3.3–4.0 ppm;

overlapped triplet and quartet), C—$CH_2$—O (4.2–4.5 ppm; triplet) and $CH_2$=C (5.7–6.7 ppm); and the areal ratios of the above absorption peaks are 3:4(2+2):2:3.

The values of elemental analysis are shown below, which agree well with the calculated values.

|  | C | H | N |
|---|---|---|---|
| Analytical value (%) | 57.23 | 7.13 | 16.78 |
| Calculated value (%) | 57.12 | 7.19 | 16.66 |

EXAMPLE 6

300 Parts of a melamine group-containing polyol of the formula

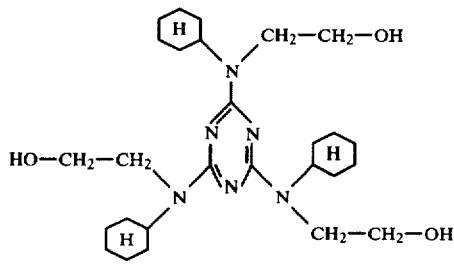

(wherein the symbol

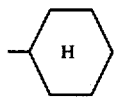

represents a cyclohexyl group) was prepared by a method similar to the Example 1 with the exception of using 429.7 parts of N-cyclohexylethanolamine in place of diethanolamine.

Using 50.5 parts of the melamine group-containing polyol obtained above, 0.03 part of p-methoxy phenol, and 41 parts of acrylic anhydride as raw materials, 62 parts of a melamine group-containing acrylate of the general formula (I) (wherein $R_{11}$, $R_{12}$ and $R_{13}$ are H; $R_{21}$, $R_{22}$ and $R_{23}$ are $CH_2.CH_2$; $R_{31}$, $R_{32}$ and $R_{33}$ are

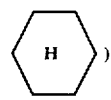)

was obtained as viscous liquid by the process similar to the Example 2.

Figure 6:
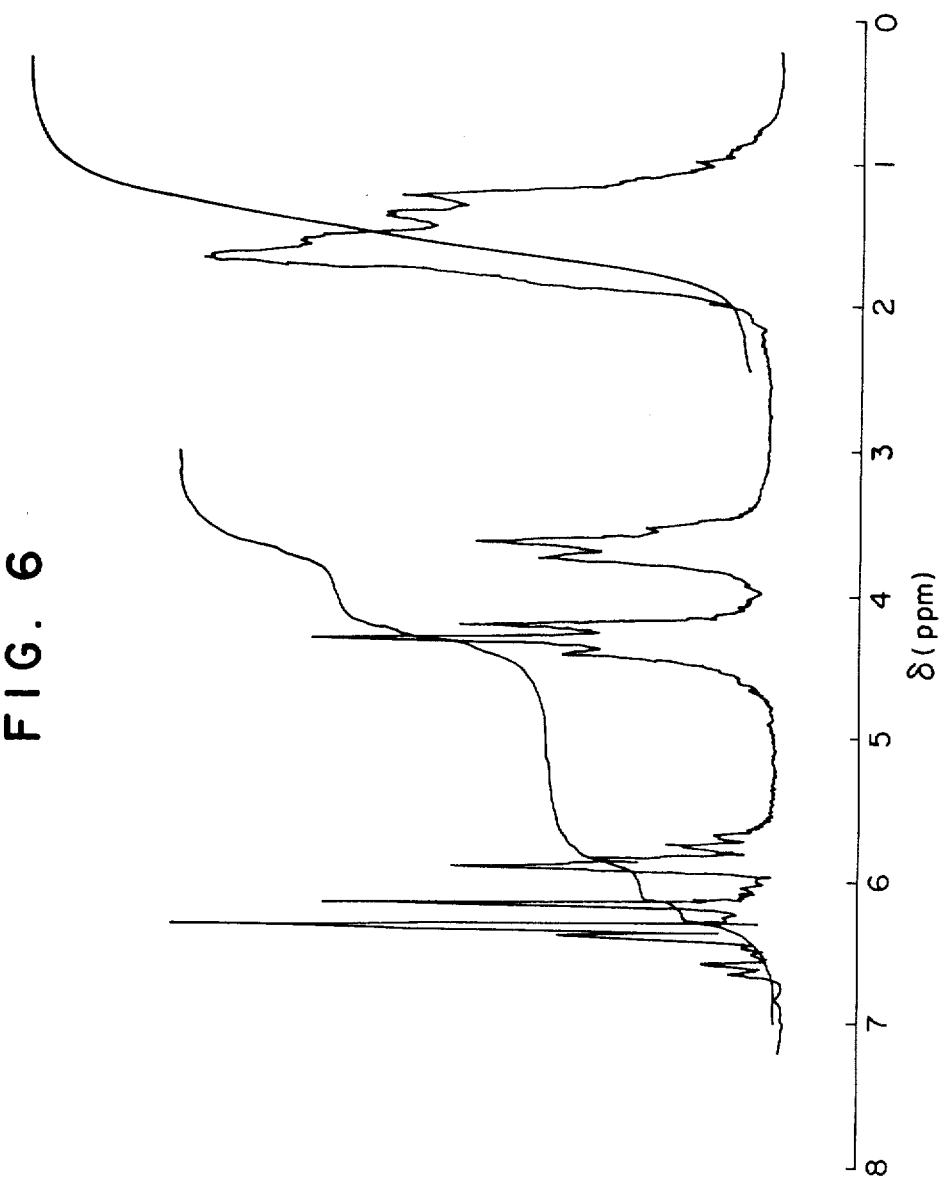
FIG. 6 is a nuclear magnetic resonance spectrum of a melamine group-containing acrylate prepared by the method of Example 6.

The infrared absorption spectrum shows characteristic absorptions of ester (1730 cm$^{-1}$), $CH_2$=CH (1620 and 1635 cm$^{-1}$), melamine (1565, 1540, 1480 and 810 cm$^{-1}$) and C—H (2870 and 2950 cm$^{-1}$). The nuclear magnetic resonance absorption spectrum given in FIG. 6 shows characteristic absorptions of methylene in cyclohexane ring (0.7–2.1 ppm), N—$CH_2$—C— (3.65 ppm; triplet), $CH_2$=CH (5.6–6.7 ppm) and overlapped absorptions of C—$CH_2$—O and methine of cyclohexyl group (4.3 ppm; triplet, and 4.0–4.8 ppm).

The values of elemental analysis are shown below, which agree well with the calculated value.

|  | C | H | N |
|---|---|---|---|
| Analytical value | 64.97 | 8.12 | 12.89 |
| Calculated value | 64.87 | 8.16 | 12.60 |

EXAMPLE 7

A polymerizable (and curable) composition was prepared by dissolving 2 parts of lauroyl peroxide in 100 parts of a melamine group-containing acrylate obtained by the process similar to the Example 1.

Said polymerizable (and curable) composition was applied to the surface of a glass plate, and cured by heating in a hot-air oven at 120° C. for 10 minutes. The cured product was optically transparent, and had a very high surface hardness. It was not soluble nor swollen in organic solvents such as methylene chloride, acetone, ethyl alcohol, methyl ethyl ketone, and toluene.

EXAMPLE 8

A polymerizable (and curable) composition composed of 100 parts of a melamine group-containing acrylate obtained by a method similar to the Example 2 and 1 part of benzoin ethyl ether was applied to a plywood laminate to 10µ thick, and cured by irradiating with a 2 KW high pressure mercury vapor lamp at a distance of 25 cm for 2 minutes. The cured product was a transparent fine coating film which scarcely marred even by the hard scrubbing with steel wool (#000). There was no change in the appearance of said cured product after immersing in hot water at 80° C. for 8 days.

EXAMPLE 9

A polymerizable (and curable) composition composed of 100 parts of a melamine group-containing methacrylate obtained by a method similar to the Example 3, 30 parts of styrene, and 1.5 parts of benzoyl peroxide was poured into a mold, and a cured cast product was obtained by heating from 55° C. to 100° C. in 5 hours. The cured product was a transparent fine article free from internal cracks and having a high surface hardness. There was no change in the appearance of said cured product after immersing in a bath of molten solder at about 280° C., revealing excellent heat resistance of the product.

EXAMPLE 10

A polymerizable (and curable) composition composed of 100 parts of melamine group-containing acrylate obtained by a method similar to the Example 4, 65 parts of methyl methacrylate, and 1.5 parts of benzoyl peroxide was poured into a space between a pair of glass plates (coated thinly with a releasing agent) parallelly disposed with a gap of 1 mm, and cured by heating from 55° C. to 100° C. in 4 hours. By disassembling the glass plates, a cured cast product was obtained.

The cured product had a smooth and hard surface, and excellent transparency.

EXAMPLE 11

A coating solution was prepared by dissolving 100 parts of a melamine group-containing acrylate obtained by a method similar to the Example 5 and 1 part of benzyl dimethyl ketal in 150 parts of methyl isobutyl ketone. A plate of polymethyl methacrylate was subjected to dip coating by dipping into said coating solution, dried in a hot-air oven at 120° C. for 2 minutes, and cured by irradiating both surfaces of the plate with a 2 KW high pressure mercury vapor lamp at a distance of 15 cm for 1 minute each. The coating film of the resin plate was about 4$\mu$ in thickness after curing, had fine and transparent appearance, and was scarcely marred even by hard scrubbing with steel wool (#000). The adhesion of the coating to the resin measured by the cross-hatch test was 100/100.

EXAMPLE 12

A polymerizable (and curable) composition was prepared by mixing 100 parts of a melamine group-containing acrylate obtained by a method similar to the Example 6, 20 parts of triallyl cyanurate and 1.5 parts of butyl perbenzoate. 100 Parts of the above polymerizable composition was incorporated with 60 parts of glass powder, and thoroughly mixed. The casting composition thus obtained was poured into a mold, pressed at 50 kg/cm$^2$ and a cured compression molded product was obtained.

The cured product had high surface hardness, excellent electrical insulation and heat resistance, and sufficiently good mechanical properties.

EXAMPLE 13

A coating solution was prepared by dissolving 40 parts of a melamine group-containing acrylate obtained by a method similar to the Example 1 and 0.4 part of benzyl dimethyl ketal in 60 parts of isopropyl alcohol. A transparent sheet of Panlite ® (a polycarbonate resin made by Teijin Chemical Co., Ltd.) having a thickness of 3 mm was subjected to dip coating by dipping into said coating solution, and dried with hot air leaving coating films each having a thickness of 5$\mu$ or both sides of the "Panlite" sheet, which were irradiated with a 2 KW high pressure mercury vapor lamp for 2 minutes (1 minute each side). The cured coating film was completely bonded and integrated with the substrate. The cured film had a pencil hardness of "H" grade, and was not marred even by the hard scrubbing with steel wool (#0000). The haze value of the coated surface was less than 3% after a mar resistance test (#80 carborundum, 500 g), whereas that of the uncoated polycarbonate was 63%.

There was no change in the appearance of the coated product after immersing in solvents such as acetone, methylene chloride, toluene, ethyl acetate, dioxane, etc., revealing high solvent resistance of the product.

EXAMPLE 14

A "Panlite" sheet having a thickness of 3 mm was dipped into a coating solution composed of 40 parts of a malamine group-containing acrylate obtained by a method similar to the Example 2, 0.4 part of benzyl dimethyl ketal, and 60 parts of ethyl cellosolve, and dried with hot air leaving a coating film having a thickness of 4$\mu$. The coated sheet was cured by ultraviolet irradiation to obtain a coated product.

The coating film and the substrate of said coated product were firmly bonded and integrated together. The surface layer was smooth and transparent, and scarcely marred even by the hard scrubbing steel wool. The haze value of the coated surface was 5.7% after a Taber abrasion test (abrasive wheel CS-10F), whereas that of the uncoated polycarbonate was 67%.

There were no changes in the appearance and physical properties of the coated product after immersing in hot water at 80° C. for 8 days, revealing high water resistance of the product.

EXAMPLES 15-18

Comparative Example 1

Four types of melamine group-containing (meth)acrylates shown in the Table 1 given below, were prepared by a method similar to the Example 1.

For comparison with the above compounds, an acrylate derived from hexamethylol melamine was prepared by the following procedures. A mixture consisting of 45.3 parts of hexamethylol melamine, 200 parts of 2-hydroxyethyl acrylate, 0.5 part of p-methoxy phenol and 8 parts of concentrated sulfuric acid, was stirred at 30° C. for 10 hours. The mixture was extracted with ethyl acetate/n-hexane mixed solvent, washed with saturated aqueous solution of sodium bicarbonate and successively with water, and the organic layer was concentrated to obtain an acrylate of the formula given below (compound A) as viscous liquid.

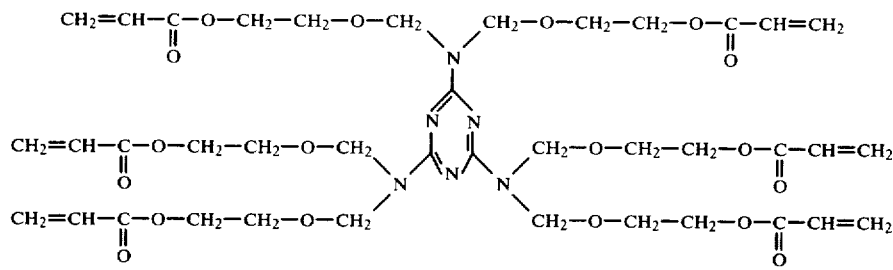

Five types of coating solutions were prepared by by adding 1 part of benzoin isobutyl ether, 40 parts of ethyl cellosolve and 20 parts of isopropyl alcohol to 40 parts of each of the five types of (meth)acrylates obtained above.

A sheet of Panlite ® (a polycarbonate resin made by Teijin Chemical Co., Ltd.) having a thickness of 3 mm was subjected to dip coating by dipping into each of the five coating solutions. After drying with hot air and curing by ultraviolet irradiation, the adhesivity, abrasion resistance and moisture resistance of each coated product were evaluated as follows:

Adhesivity: Cross-hatch test,
Abrasion resistance: Mar resistance test (JIS T-8147)
Haze value (%) after dropping 500 g of carborundum (#80),
Moisture resistance: Appearance and abrasion resistance were evaluated after being left to stand at 50° C. and RH 100% for 20 days.

The evaluation grades are as follows;
Grade 1. No or little changes in both of the appearance and the abrasion resistance.
Grade 2. No change in the appearance and a little deterioration in the abrasion resistance.
Grade 3. No change in the appearance and deterioration in the abrasion resistance.
Grade 4. Changes take place in both of the appearance and the abrasion resistance.
Grade 5. Substantial changes in both of the appearance and the abrasion resistance.

dipping into the above coating solution, dried with hot air at 100° C. and cured by heating at 150° C.

The coating layer thus obtained had excellent adhesivity with the substrate, and its surface was scarcely marred even by the hard scrubbing with steel wool. The degree of evaluation of the coating layer was 2.

The pencil hardness and the haze value after mar resistance test (#80 carborundum, 500 g) of diethylene glycol bis(allyl carbonate) were remarkably improved from 3H and 21%, respectively, of the uncoated surface to 6H and 3.2% of the coated surface prepared by the above treatment.

EXAMPLE 20

A coating solution composed of 50 parts of a melamine group-containing acrylate prepared by a method similar to the Example 1, 0.5 part of benzyl dimethyl ketal, and 50 parts of methyl isobutyl ketone, were applied to the surface of a biaxially oriented polyethylene terephthalate film having a thickness of 75μ and longitudinal and transverse draw ratios of 3 using a bar coater (#5), dried with hot air at 120° C., and cured by the ultraviolet irradiation with a 2 KW high pressure mercury vapor lamp. The cured layer had a thickness of 3 mm and its adhesivity with the substrate was excellent. The surface of the coating layer had a pencil hardness of 4H, and was not marred by the hard scrubbing with steel wool (#0000). The haze value of the coated film after the mar resistance test (#80 carborundum, 500 g) was less than 3%, whereas that of the uncoated poly-

TABLE 1

| | $R_{11}$, $R_{12}$ and $R_{13}$ of the above general formula (I) | $R_{21}$, $R_{22}$ and $R_{23}$ of the above general formula (I) | $R_{31}$, $R_{32}$ and $R_{33}$ of the above general formula (I) | Adhesivity | Abrasion resistance Haze (%) | Moisture resistance |
|---|---|---|---|---|---|---|
| Example 15 | —CH$_3$ | —CH$_2$.CH$_2$.CH$_2$.CH$_2$— | —CH$_2$—⟨phenyl⟩ | Good | 6.0 | 1 |
| Example 16 | —H | —CH$_2$.CH$_2$.CH$_2$.CH$_2$.CH$_2$.CH$_2$— | —H | Good | 4.9 | 2 |
| Example 17 | —H | —CH$_2$.CH$_2$— | —CH$_2$.CH$_3$ | Good | 4.6 | 1 |
| Example 18 | —H | —CH$_2$.CH$_2$— | —⟨H⟩ | Good | 5.9 | 1 |
| Comparative example 1 | | Compound A | | Good | 3.2 | 5 |

 represents a cyclohexane ring.

EXAMPLE 19

A coating solution composed of 40 parts of a melamine group-containing acrylate obtained by the method of the Example 1, 1 part of lauroyl peroxide and 60 parts of methyl isobutyl ketone was prepared. A sheet having a thickness of 2 mm and made of diethylene glycol bis(allyl carbonate) was subjected to dip coating by ethylene terephthalate film was between 50 and 60%.

EXAMPLE 21

A coating liquid composed of 50 parts of a melamine group-containing acrylate prepared by a method similar to the Example 2, 0.5 part of benzyl dimethyl ketal, and 50 parts of isopropyl alcohol, was applied to an unoriented polyethylene terephthalate film (250μ thick), dried at 50° C., and cured by ultraviolet irradiation to obtain a polyester formed product having a coating layer of 3μ thickness. The coating layer and the substrate of the formed product were firmly bonded and integrated together. The formed product was smooth and transparent, and scarcely marred even by the hard scrubbing with steel wool. The haze value after mar resistance test (500 g) was 3-4%. There were no changes in the appearance and properties of the coated product after immersion into hot water at 80° C. for 8 days. The coated surface of the film was not attacked by organic solvents such as acetone, methylene chloride, toluene, dioxane, etc., and kept its transparency, whereas the polyester-side surface of the coated film was attacked by the above solvents causing loss of clarity.

EXAMPLES 22-25

Comparative Example 2

Four types of melamine group-containing (meth)acrylates shown in the Table 2 given below, were prepared by a method similar to the Example 1.

The compound A defined in the Comparative example 1 is prepared by the method described in said example.

Five types of coating solutions were prepared by adding 1 part of benzoin isobutyl ether and 50 parts of methyl isobutyl ketone to 50 parts of each of the five types of (meth)acrylate obtained above.

Each of said coating solutions was applied to an oriented polyethylene terephthalate film having a thickness of 100μ (draw ratios: 3 times both to longitudinal and transverse directions) using a bar coater (#5), dried with hot air at 120° C., and cured by ultraviolet irradiation. The adhesivity, abrasion resistance, and moisture resistance of each coated product were evaluated according to the methods described in the Examples 15-18.

wool (#0000), and the evaluation degree of the moisture resistance was 2.

What we claimed are:

1. A melamine group-containing (meth)acrylate of the following formula:

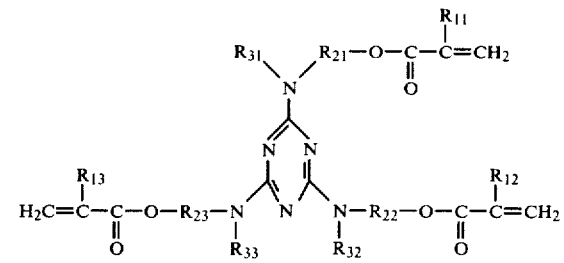

wherein $R_{11}$, $R_{12}$ and $R_{13}$ are each hydrogen atom or methyl group; $R_{21}$, $R_{22}$ and $R_{23}$ are each an alkylene group of from 2 to 10 carbon atoms, in which the number of carbon atoms in the main chain is 2 or more; and $R_{31}$, $R_{32}$ and $R_{33}$ are each hydrogen atom, an aliphatic, alicyclic or aromatic hydrocarbon group of from 1 to 10 carbon atoms, or a group of the following formula:

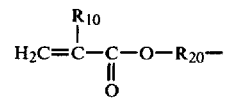

wherein $R_{10}$ is hydrogen atom or methyl group; and $R_{20}$ is an alkylene group of from 2 to 10 carbon atoms, in which the number of carbon atoms in the main chain is 2 or more.

2. A melamine group-containing (meth)acrylate of claim 1, wherein $R_{20}$, $R_{21}$, $R_{22}$, and $R_{23}$ of the formula are each an alkylene group of from 2 to 6 carbon atoms, in which the number of carbon atoms in the main chain is 2 or more; and $R_{31}$, $R_{32}$, and $R_{33}$ of the formula are each hydrogen atom, an aliphatic, alicyclic or aromatic

TABLE 2

| | $R_{11}$, $R_{12}$ and $R_{13}$ of the above general formula (I) | $R_{21}$, $R_{22}$ and $R_{23}$ of the above general formula (I) | $R_{31}$, $R_{32}$ and $R_{33}$ of the above general formula (I) | Adhesivity | Abrasion resistance Haze (%) | Moisture resistance |
|---|---|---|---|---|---|---|
| Example 22 | —CH₃ | —CH₂.CH₂.CH₂.CH₂— | —CH₂—⟨ ⟩ | Good | 6.0 | 1 |
| Example 23 | —H | —CH₂.CH₂.CH₂.CH₂.CH₂.CH₂— | —H | Fair | 4.7 | 2 |
| Example 24 | —H | —CH₂.CH₂— | —CH₂.CH₃ | Good | 4.5 | 1 |
| Example 25 | —H | —CH₂.CH₂— | —⟨H⟩ | Good | 5.7 | 1 |
| Comparative example 2 | | Compound A | | Good | 3 | 5 |

⟨H⟩ represents a cyclohexane ring.

EXAMPLE 26

A coating solution composed of 50 parts of a melamine group-containing acrylate obtained by a method similar to the Example 1, 1 part of lauroyl peroxide, and 50 parts of isopropyl alcohol, was applied to a polybutylene terephthalate sheet, dried at 120° C., and cured at 150° C.

The coated surface of the polyester sheet was scarcely marred even by the hard scrubbing with steel hydrocarbon group of from 1 to 8 carbon atoms, or a group of the following formula:

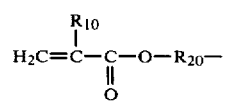

wherein $R_{10}$ is hydrogen atom or methyl group; and $R_{20}$ is a group defined above.

3. A melamine group-containing (meth)acrylate of claim 1, wherein $R_{31}$, $R_{32}$ and $R_{33}$ contain 1–8 carbon atoms.

4. A melamine group-containing (meth)acrylate of claim 3, wherein $R_{31}$, $R_{32}$ or $R_{33}$ are substituted with halogen.

* * * * *